United States Patent [19]

Parker et al.

[11] Patent Number: 4,576,173
[45] Date of Patent: Mar. 18, 1986

[54] ELECTRO-OPTICAL DEVICE AND METHOD FOR MONITORING INSTANTEOUS SINGLET OXYGEN CONCENTRATION PRODUCED DURING PHOTORADIATION USING A CW EXCITATION SOURCE

[75] Inventors: John G. Parker, Olney; William D. Stanbro, Columbia, both of Md.

[73] Assignee: The Johns Hopkins University, Baltimore, Md.

[21] Appl. No.: 629,854

[22] Filed: Jul. 11, 1984

Related U.S. Application Data

[63] Continuation-in-part of Ser. No. 393,188, Jun. 28, 1982.

[51] Int. Cl.$^4$ ............................ A61B 6/00; A61N 5/00
[52] U.S. Cl. ...................................... 128/633; 128/634; 128/654; 128/664; 128/362; 128/635
[58] Field of Search ............................ 128/362, 395, 303.1, 128/633, 634, 654, 665, 396-398, 664, 635

[56] References Cited

U.S. PATENT DOCUMENTS 3,136,310  6/1964  Meltzer ............................ 128/634
4,336,809  6/1982  Clark ................................ 128/665

OTHER PUBLICATIONS

Kinsey et al., Rev. of Scien. Instru., vol. 51 (10), Oct. 1980, pp. 1403-1406.
Doiron et al., Chest, vol. 76:1, Jul. 1979, pp. 27-32.
Dougherty et al., Cancer Research, vol. 38, Aug. 1978, pp. 2628-2635.
Parker et al., J. Amer. Chem. Soc., vol. 104, 1982, pp. 2067-2069.
Krasnovsky, Biofizaka, vol. 21: No. 4, 1976, pp. 770-771.
Khan et al., Proc. Natl. Acad. Science, vol. 76 (12), Dec. 1979, pp. 6047-6049.
Salokhiddinov et al., Chem. Phys. Letters, vol. 76, No. 1, Nov. 15, 1980, pp. 85-86.
Krasnovsky, Photochemistry and Photobiology, vol. 29, 1979, pp. 29-36.
Seddon et al., Int. J. Radiat. Phys. Chem., vol. 5, 1973, pp. 323-328.
Parker et al., Presentation, Clanton Foundation, Symposium, Apr. 24-28, 1983.

*Primary Examiner*—Kyle L. Howell
*Assistant Examiner*—John C. Hanley
*Attorney, Agent, or Firm*—Robert E. Archibald; Howard W. Califano

[57] ABSTRACT

A method and apparatus is disclosed for optically monitoring the concentration of singlet oxygen produced during photoradiation. A composite optical emission in the 1.27 micron frequency band is detected and electrically processed to separate a first component due to the decay of singlet oxygen from a second unwanted component due to the fluorescence of the photosensitizing dye.

A chopped CW excitation source is used to excite the photosensitizing dye and a signal processing means such as a lock-in amplifier is used to separate the singlet oxygen emission component which appears out of phase from the chopped excitation signal and the in-phase photosensitizer fluorescence.

The magnitude and/or other characteristics of the singlet oxygen emission component can be used to determine properties of complex biological or other media. In a therapeutic environment the magnitude and/or other characteristics of the singlet oxygen emission can be used by the treating physician to set a therapeutic light dosimetry.

38 Claims, 10 Drawing Figures

ELECTRO-OPTICAL DEVICE AND METHOD FOR MONITORING INSTANTEOUS SINGLET OXYGEN CONCENTRATION PRODUCED DURING PHOTORADIATION USING A CW EXCITATION SOURCE

STATEMENT OF GOVERNMENTAL INTEREST

The Government has rights in this invention pursuant to Contract No. N00024-81-C-5301 awarded by the Department of the Navy.

CROSS-REFERENCE TO RELATED APPLICATION

This is a continuation-in-part of patent application, Ser. No. 393,188, filed on June 28, 1982.

BACKGROUND OF THE INVENTION

1. Field of the Invention

This invention relates to an apparatus and method for monitoring the instantaneous concentration of singlet oxygen produced during photoradiation when a CW excitation source is used to excite a photodynamic sensitizer and also the means for processing the resultant data.

2. Background and Technical Summary

When certain non-toxic photodynamic sensitizers, such as hematoporphyrin derivative (HPD) and components thereof, are injected intravenously into the human body, they are selectively retained by cancerous tissue. Thus, two or three days after injection, significantly higher levels of the photodynamic sensitizer are retained in malignant tissue. The selective retention of hematoporphyrin derivative by cancerous tissue was first used clinically as a diagnostic tool. In the presence of ultraviolet or shortwave length visible light, such tissue will exhibit a bright red fluorescence while normal tissue appears light pink. A discussion of clinical investigations using this diagnostic technique can be found in an article entitled "Hematoporphyrin Diacetate: A Probe to Distinguish Malignant from Normal Tissue by Selective Fluorescence" by R. W. Henderson, G. S. Christie, P. S. Clezy and J. Lineham, *Brit.J. Exp. Pathol.*, Vol. 61, pages 325-350 (1980). Another reference by D. R. Doiron and A. E. Profio entitled "Laser Fluorescence Bronchoscopy for Early Lung Cancer Localization" published in *Lasers in Photomedicine and Photobiology* (1980) teaches the use of a laser fluorescence bronchoscope to detect and localize small lung tumors by observing this red fluorescence.

An additional clinical application has recently been found in the treatment and destruction of malignant tissue, this treatment being referred to variously as photochemotherapy, photodynamic therapy or photoradiation therapy all of which are to be considered equivalent. The overall process by which biological damage occurs as the result of optical excitation of the photodynamic sensitizer in the presence of oxygen, is generally referred to as "photodynamic action". As indicated above, photochemotherapy involves the intravenous injection of a sensitizer derived from hematoporphyrin into the patient. After the passage of several days, usually three, the HPD sensitizer (or components thereof) is retained in significant amounts by cancerous tissue, however being eliminated by healthy tissue. The tumor is then exposed to a therapeutic light and this light energy causes the photodynamic sensitizer to be excited to an energetic metastable triplet state. Through a direct intermolecular process, the sensitizer transfers this energy to oxygen molecules present in the tissue and raises them from the ground triplet to the first excited electronic singlet state, $^1O_2$ [symbolic designation of molecular oxygen in the $^1\Delta_g$ electronic state]. The singlet oxygen, $^1O_2$, attacks and functionally destroys the cell membranes ultimately inducing necrosis and destroying the cancerous tissue.

In an article by Thomas J. Dougherty et al entitled "Photoradiation Therapy for the Treatment of Malignant Tumors" published in *Cancer Research*, Vol. 38, pages 2628-2635 (1978), problems associated with prescribing the correct therapeutic light dosages are discussed. If the dosage is too weak, the tumor response will be partial or incomplete. If the irradiation time is too long or intensity too high, normal skin or tissue will experience necrosis. The aforementioned article points out the difficulty of determining the correct therapeutic dosage of light. This problem has been proven to be quite significant and currently is one of the major hurdles that must be overcome before photochemotherapy can be used to treat tumors in a systematic and reliable fashion.

Other clinical applications of photoradiation therapy are being investigated which also point out the urgent need to develop an apparatus and method for monitoring the instantaneous generation of singlet oxygen.

SUMMARY OF THE INVENTION

The inventors recognized the need to measure the levels of singlet oxygen generated in a biological environment during photoradiation therapy. They recognized that adequate photoradiation treatment is questionable unless one knows directly the rate at which singlet oxygen is generated in the biological or malignant tissue. The inventors recognized that the generation of singlet oxygen involves several key factors: (1) the therapeutic light source must be of the proper intensity and wavelength sufficient to elevate the photodynamic sensitizer to an excited triplet state; (2) there must be a sufficient concentration of oxygen localized within the tumor both initially and during the period of irradiation to be excited by energy transfer from the sensitizer; (3) the local sensitizer concentration may vary considerably, depending on the hydrophobic or hydrophilic nature of the immediate environment; and (4) the rate of quenching of $^1O_2$ may vary substantially with the existing medium, being generally more rapid in an aqueous than in a lipid environment. Therefore, merely measuring the incident light intensity and time of exposure, as is taught by the prior art, will not supply adequate information regarding the generation of singlet oxygen within the tumor tissue. The inventors, therefore, recognize the need to determine directly the amount of singlet oxygen which is being generated during photoradiation therapy.

The inventors recognize that direct monitoring of the generation of $^1O_2$ is possible because in the interaction of singlet oxygen molecules with the surrounding medium, the singlet oxygen molecules undergo a collisionally-induced radiative transition to the ground triplet state emitting light in a narrow band centered at a wavelength in the proximity of 1.27 microns, e.g., J. G. Parker and W. D. Stanbro, "Optical Determination of the Collisional Lifetime of Singlet Molecular Oxygen $[O_2(^1\Delta_g)]$ in Acetone and Deuterated Acetone", *J.Am.-Chem.Soc.*, Vol. 104, pp 2067-2069 (1982).

Singlet oxygen emission in liquids was first described in an article by A. A. Krasnovsky, Jr. entitled "Photosensitized Luminescence of Singlet Oxygen in Solution" reprinted in *Biophysics* (GB), Vol. 21, page 770 (1976). Krasnovsky is generally recognized as the first to identify and optically detect the singlet oxygen emission at 1.27 microns in solution. Krasnovsky used a cryogenically cooled photomultiplier as the means for detecting this emission in a $CCl_4$ solvent. Additional work has been done for various other solvents, e.g., A. H. Khan and M. Kasha, "Direct Spectroscopic Observation of Singlet Oxygen Emission at 1268 nm, Excited by Sensitizing Dyes of Biological Interest in Liquid Solution", *Proc. Natl. Acad. Scie.*, Vol. 76(12), page 6047 (1979); and K. I. Salokhiddinov, B. N. Dzhagarov, I. M. Byteva, and G. P. Gurinovich, "Photosensitized Luminescence of Singlet Oxygen in Solutions at 1588 nm", *Chem. Phys. Lett.*, Vol. 76(1), page 85 (1980). To detect the 1.27 micron emission, Khan et al used a near-infrared spectrophotometer that employed a thermoelectrically cooled lead sulfide detector and Salokhiddinov et al used a liquid nitrogen cooled germanium photodiode.

However, these prior researchers measured the singlet oxygen emission in solvents such as carbon tetrachloride $CCl_4$ where the lifetime of singlet oxygen is extremely long—approximately 28,000 microseconds. The more difficult problem, which the present inventors have addressed, is how to optically detect and electronically process singlet oxygen emissions generated in a biological environment. In a biological environment, composed essentially of water and lipids (hydrocarbons), the singlet oxygen lifetime is relatively short, ranging from 3 (water) to 30 (lipid) microseconds. The present invention provides an apparatus and method for detecting the singlet oxygen emission produced during photoradiation therapy in such a biological environment.

To fully understand the problem, it is essential to recognize that both the photodynamic sensitizer and the singlet oxygen molecules produce emissions having wavelengths in the region of 1.27 microns. Results of experimental measurements made by the present inventors indicate that the singlet oxygen emission and the sensitizer infrared fluorescence both arise as a consequence of optical excitation of the sensitizer and are inextricably intertwined. Therefore, a composite two component emission is produced having: (1) a first spectrally discrete component attributed to singlet oxygen emissions; and (2) a second spectrally diffuse component produced by fluorescence of the sensitizer. Even if a narrow band pass filter centered at 1.27 microns were used, both the sensitizer fluorescence and the singlet oxygen emission would be transmitted to the photodetector. The desired singlet oxygen emission signal thus *cannot be spectrally separated* from the composite sensitizer fluorescence/singlet oxygen emission signal. (The infrared fluorescence produced by the sensitizer ranges in wavelength from 0.7 microns to wavelengths in excess of 1.50 microns).

The central difficulty to be overcome, therefore, in monitoring the singlet oxygen emission is to separate the singlet oxygen emission component from the component due to sensitizer infrared fluorescence. To accomplish this task one must exploit the different nature of the two signal components. The inventors have found that the sensitizer fluorescence appears and disappears essentially simultaneously with the switching on or switching off of the excitation light, while the appearance and disappearance of the singlet oxygen emission is delayed in time. The inventors discovered that the delay is due to the fact that formation of singlet oxygen is *not* directly coupled to the optical excitation. Rather, formation of singlet oxygen involves a collisional transfer of energy from the sensitizer metastable triplet state, and is thus delayed with respect to the initiation of the optical excitation by the time required to bring about collision of the ground electronic state dissolved oxygen $^3O_2$ with the excited photodynamic sensitizer.

The problem of extracting the singlet oxygen emission signal from the composite sensitizer fluorescence/singlet oxygen emission signal, is extremely complex in a biological environment. First, the sensitizer fluorescence can be much larger than the singlet oxygen emission, e.g., having a magnitude 20 times that of the singlet oxygen emission in an aqueous environment. The weakness of the singlet oxygen emission in this environment is attributed to the short lifetime of singlet oxygen. In lipid environments, the $^1O_2$ lifetimes are slightly longer and the magnitudes of the infrared fluorescence component tends to be relatively smaller. Secondly, the time delay between the sensitizer fluorescence and the singlet oxygen emission is dependent on the diffusion rate of $^3O_2$ for each particular solvent. In a biological environment comprised of essentially water and lipids, the delay varies from 2–3 μsec. for water to times approaching 10 μsec for glycerol and ethylene glycol (characteristic of cell membrane environments) and various blood serums.

Therefore, in a biological medium, the sensitizer fluorescence is in general much larger in magnitude than the singlet oxygen emission; the time delay between the appearance of the sensitizer fluorescence and the maximum singlet oxygen emission is short (2.5 to 10.0 microseconds); and, the overall lifetime of singlet oxygen can be extremely short (e.g., 3.2 μsec. in aqueous regions).

The inventors recognized that, in such a biological environment, if one merely measures magnitude of the optical emission in a narrow band centered at 1.27 microns (i.e., the singlet oxygen emission band), one will essentially be measuring a fluorescent signal generated by the sensitizer and *not* the singlet oxygen emission.

The present inventors have developed a method and apparatus for extracting the singlet oxygen emission signal from the composite sensitizer fluorescence/singlet oxygen emission signal, both of which appear in the 1.27 micron singlet oxygen emission band. The invention generally includes: a means for chopping a CW (substantially constant intensity) excitation source (chopping frequency $f_c$ ranging from 1 kHz to 100 kHz) which is used to illuminate a biological mass which has absorbed a photodynamic sensitizer such as hematoporphyrin derivative; an optical detection means including a light collecting means, filter means and photodetector means all for detecting the *composite* emission signal produced in the 1.27 micron singlet oxygen emission band; and, a signal processing means including a lock-in amplifier, connected to the photodetector and triggered at the chopped rate of the excitation signal. The signal processing means processes the composite signal so as to extract the singlet oxygen signal from the composite sensitizer fluorescent/singlet oxygen emission signal.

The inventors discovered that the composite sensitizer fluorescence/singlet oxygen emission signal can be resolved in the frequency domain into a real component and a quadrature (or imaginary) component. The real component (where phase angle relative to the chopped *incident* light equals zero—degrees) corresponds to a signal which is dominated by the sensitizer fluorescence. However, the quadrature component (where phase angle $\phi = -90°$) is only related to the singlet oxygen emission signal. This breakthrough enables the present invention to isolate and detect the singlet oxygen emission signal produced during photoradiation therapy when a CW excitation source is utilized.

The inventors also discovered that adjusting the chopping frequency $f_c$ allows one to further discriminate in the frequency domain between the singlet oxygen emission produced in different media, i.e., a maximum singlet oxygen quadrature component produced in an aqueous environment can be distinguished from a maximum singlet oxygen quadrature component produced in a lipid environment. Similarly, scanning the chopping frequency $f_c$ across a desired frequency range can be used, in a heterogeneous environment having more than one component, to obtain the maximum singlet oxygen quadrature signal.

The present inventors thus recognized that optical excitation of the photodynamic sensitizer during photoradiation therapy produces a composite two-component signal; a first component due to the spectrally discrete singlet oxygen emission and a second larger component due to the spectrally diffuse sensitizer infrared fluorescence. Recognizing that a narrow bandpass filter, centered to pass the 1.27 micron signal oxygen emission band, will pass both the desired singlet oxygen emission signal and the stronger undesired signal due to the sensitizer fluorescence, the present inventors have developed an apparatus and method for isolating the singlet oxygen emission signal by frequency domain signal processing.

One novel feature of the invention is the use of a signal processing means for processing the composite sensitizer fluorescence/singlet oxygen emission signal produced during photoradiation therapy and separating the out of phase singlet oxygen signal component from the sensitizer infrared fluorescence component which is essentially in phase with the incident chopped CW excitation light.

A second novel feature is the use of a *chopped CW excitation* in combination with a signal processor. The excitation must be chopped while the singlet oxygen level is being determined and the signal processor is triggered at the chopping rate, in order to separate the out of phase singlet oxygen emission from the composite signal dominated by the sensitizer fluorescence.

A third novel feature of the invention is the recognition that the quadrature component (the component along the imaginary axis of a phase diagram, where phase angle $\phi = -90°$, i.e., 90° out of phase with respect to the incident chopped CW excitation) provides the maximum separation of the singlet oxygen emission signal from the sensitizer fluorescent signal. The inventors have discovered that the quadrature component (phase $\phi = -90°$) is based on a vectorial component produced by the singlet oxygen signal.

A fourth novel feature of the present invention involves tuning the chopping frequency ($f_c$) to obtain the maximum quadrature singlet oxygen emission. The chopping frequency ($f_c$) which maximizes the singlet oxygen quadrature component is dependent on the singlet oxygen quenching time ($Y_D$) for a particular medium. This relationship, which is developed in detail later, is summarized in the following equation:

$$f_c(\max) = f_m \frac{1}{2\pi T_D}$$

Since in a complex biological environment the ratio of aqueous to lipid concentrations may vary substantially, measurement of the singlet oxygen component at a plurality of chopping frequencies or scanning through a range of frequencies will assure a maximum signal reading.

A fifth novel feature of the invention is the adjustment of the chopping frequency to discriminate in the frequency domain between the maximum singlet oxygen signal generated in different media. In a biological mass, generally containing both aqueous and lipid components, the chopping frequency could be set at one rate to determine the maximum concentration of singlet oxygen generated in lipid regions and it could be set to another rate to determine the maximum concentration of singlet oxygen generated in aqueous regions.

A sixth novel feature of the invention is that it provides a means for remotely monitoring the instantaneous singlet oxygen concentration produced during photoradiation therapy when a CW light source acts as the excitation. By monitoring the singlet oxygen level, the physician or operator can adjust the therapeutic irradiation conditions (i.e., intensity, wavelength, angle of incidence, time of exposure, etc.) to provide a singlet oxygen level as necessary to satisfy predetermined clinical conditions.

DESCRIPTION OF THE PREFERRED EMBODIMENTS

Figure 1:
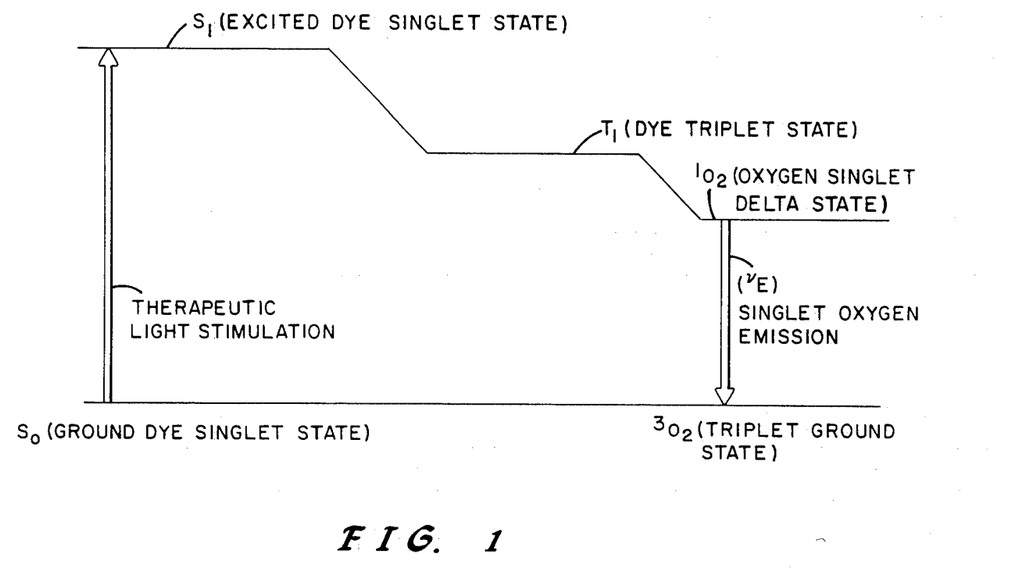
FIG. 1 is a diagram illustrating the overall system kinetics, showing the CW excitation light stimulating a photodynamic sensitizer and the resulting generation of singlet oxygen.

Photoradiation therapy involves injecting a patient with a photodynamic sensitizer, such as hematoporphyrin derivative, and after the sensitizer has localized at the appropriate biological site, illuminating that site with optical energy. The resulting photodynamic action causes singlet oxygen to be generated in a two-step process. FIG. 1 illustrates schematically the overall system kinetics. First the photodynamic sensitizer is excited from the ground state, $S_0$, to the first excited electronic state, $S_1$, by means of a therapeutic light source, such as CW laser radiation at 6300 angstroms (red light). The dye singlet state $S_1$ is then transformed via an intramolecular coupling to the lowest-lying dye triplet state, $T_1$, as indicated in the figure. Subsequent deactivation of this triplet state to the ground singlet state, $S_0$, in the absence of oxygen, is forbidden by the spin selection rules, resulting in lifetimes of this particular species under anaerobic (oxygen-excluded) conditions as long as one millisecond. However, in the presence of oxygen localized in the tissue, the dye triplet, $T_1$, will deactivate rapidly (1 to 10 sec) to the dye singlet ground state, $S_0$, in a spin-conserving intermolecular process in which essentially all the energy in the dye triplet is transferred to the triplet electronic state of oxygen, $^3O_2$, raising the oxygen to the first excited electronic singlet state, $^1O_2$, approximately 1 electron-volt above the ground state. This spin-conserving energy transfer is possible only because the ground electronic state of molecular oxygen happens to be a triplet which is not true for most stable molecules. This energy transfer, which is shown in FIG. 1, can be represented as follows:

$$T_1 + {}^3O_2 \rightarrow S_0 + {}^1O_2 \quad (1)$$

When singlet oxygen, $^1O_2$, interacts with molecules contained in the surrounding medium M, a relatively weak collisionally induced emission occurs:

$$^1O_2 + M \rightarrow {}^3O_2 + M + h\nu_E \quad (2)$$

The quantity $\nu_E$ is the frequency associated with the center of the emission band frequency and corresponds a wavelength of 1.27 microns. (The singlet oxygen emission band is centered at 1.27 microns and has a full-width-at-half-maximum (FWHM) of 0.02 microns extending from 1.26 microns—1.28 microns. This band shall hereafter be referred to as the singlet oxygen 1.27 micron emission band or the 1.27 micron band.) By optically detecting and monitoring this emission it is possible to determine the instantaneous rate at which singlet oxygen is being generated and is attacking biological matter.

Figure 2:
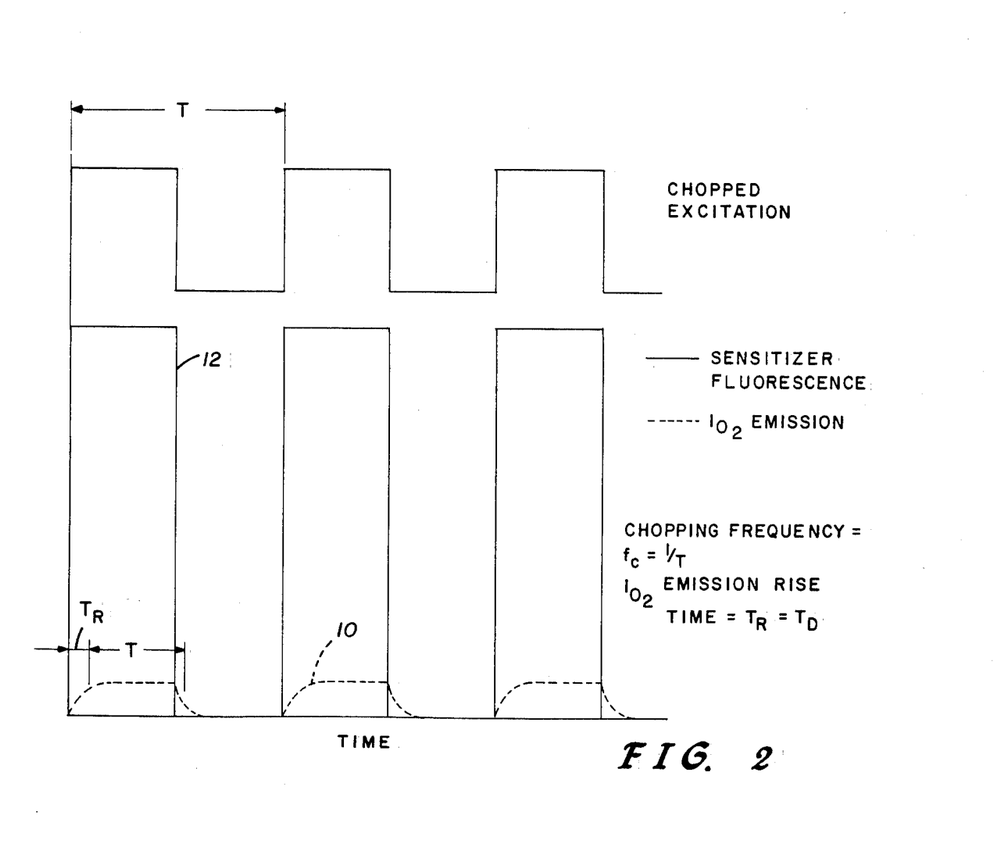
FIG. 2 is a graph showing the composite sensitizer fluorescence/singlet oxygen emission signal appearing in the 1.27 micron band.

The optical energy emitted in the 1.27 micron emission band during photodynamic therapy is a composite signal comprising a first component due to the spectrally diffuse fluorescence of the sensitizer and, a second component produced by the spectrally discrete emission from singlet oxygen molecules. FIG. 2 illustrates the composite signal in the 1.27 micron band. Both the singlet oxygen ($^1O_2$) emission (10) and the sensitizer fluorescence (12) arise as a consequence of optical excitation and both are inextricably intertwined in the 1.27 micron emission band. There is no way of spectrally separating the singlet oxygen emissions from the sensitizer fluorescence - both appearing in the 1.27 micron singlet oxygen emission band. The sensitizer fluorescence in the 1.27 micron band also is generally much larger in magnitude than the relatively weak singlet oxygen emissions.

The central difficulty to be overcome, therefore, in monitoring the singlet oxygen emission is to separate this component from that due to the sensitizer fluorescence. Applicants have discovered that the composite signal can be separated by signal processing using a lock-in amplifier synchronous detector, or similar processor. This processing utilizes the fact that the sensitizer fluorescence is simultaneous with the exciting light while the appearance of the singlet oxygen emission is delayed in time. This time delay is due to the fact that formation of the singlet oxygen is not directly coupled to the optical excitation. Formation of $^1O_2$ involves a collisional transfer of energy from the sensitizer metastable triplet state, thus delayed with respect to the initiation of the optical excitation by the time required to bring about collision of the ground electronic state dissolved oxygen $^3O_2$ with the excited sensitizer. This collision time is dependent on the diffusion rate of $^3O_2$ in the particular medium, as well as the ambient $^3O_2$ concentration level (i.e., $^3O_2$ solubility). Some media are characterized by high oxygen solubility and diffusion rates (e.g., ethanol, methanol, acetone) with characteristic sensitizer triplet energy transfer times in the range of 0.20–0.30 $\mu$sec; however, others notably $H_2O$ and $D_2O$, involve significantly longer times (2–3 $\mu$sec) and in the extreme cases of high solvent viscosity (i.e., low diffusion rates) and low oxygen solubility, times of the order of 10 sec are involved (e.g., ethylene glycol).

Absorption of the incident optical excitation energy leads to the essentially instantaneous formation of an initial sensitizer triplet concentration $[T_1]_0$. Transfer of this energy to the ground triplet state oxygen takes place according to Eq.(1) appearing above.

Quantitatively, Equation (1) may be expressed in the following form:

$$\frac{d[T_1]}{dt} = \alpha J - K_T[{}^3O_2][T_1] \quad (3)$$

where $J=J(t)$ is the time-dependent incident light flux expressed in photons/cm$^2$ second, $\alpha$ is the sensitizer absorption coefficient expressed in cm$^{-1}$. In most cases depletion of ground state oxygen is unimportant, i.e., $[^1O_2] << [^3O_2]$, in which case Eq. (3) may be written:

$$\frac{d[T_1]}{dt} = \alpha J - k_T[T_1] \quad (4)$$

in which $$k_T = K_T[{}^3O_2] \quad (5)$$

represents the rate of transfer of energy from the sensitizer triplet to $^3O_2$ to form $^1O_2$. The rate of increase of $[^1O_2]$ is given by the following equation:

$$\frac{d[{}^1O_2]}{dt} = k_T[T_1] - k_D[{}^1O_2] \quad (6)$$

with $k_D$ denoting the rate of loss of $^1O_2$ due to collisions with the solvent molecules (or molecular complexes).

For CW optical excitation, it is necessary to chop the *incident* light to facilitate the required *separation* of sensitizer fluorescence and singlet oxygen emission. In this case, the fundamental fourier components of [T₁] and [¹O₂] are given by equations (7) and (10). Replacement of the time derivative in Eq. (3) by jw and setting $J = J_o \cdot e^{jwt}$ gives $$[T_1] = \frac{\alpha J_o}{(k_T + j\omega)} \quad (7)$$

where $w = 2\pi$ times the chopping frequency $f_c$ of the excitation light.

Further, Eq. (6) becomes $$[^1O_2] = \frac{k_T[T_1]}{(j\omega + k_D)} \quad (8)$$

Combination of Eqs. (7,8) gives:

$$[^1O_2] = \frac{(\alpha J_o)\tau_D}{(1 + j\omega\tau_T)(1 + j\omega\tau_D)} \quad (9)$$

in which $\tau_T = 1/k_T$, $\tau_D = 1/k_D$.

Further setting $[T_1]_o = [\alpha J_o]\tau_D$ we obtain $$[^1O_2] = \frac{[T_1]_o}{(1 + j\omega\tau_T)(1 + j\omega\tau_D)} \quad (10)$$

The magnitude of the singlet oxygen emission at 1.27 micron will then be proportional to [¹O₂] and thus to the amplitude of the exciting light intensity $J_o$. The magnitude of the sensitizer fluorescence component will also be proportional to $J_o$, with a coefficient which, however, is different from that quantifying the ¹O₂ emission. In general terms, we thus express the total fundamental fourier component of the detector output generated by the combined emission components to be:

$$E_D = A + B[^1O_2] \quad (11)$$

where the constants A and B depend, in addition to the common incident light intensity, on optical and electronic parameters characterizing the detector input system. The ratio A/B will depend primarily on the optical input filter and detector sensitivity characteristics, being independent, however, of the nature of the detector preamplifier. If, referring to Eq. (11), we write:

$$[^1O_2] = [^1O_2]_R - j[^1O_2]_I, \quad (12)$$

in which $[^1O_2]_R$ and $[^1O_2]_I$ represent, respectively, the magnitudes of the real and imaginary components of [¹O₂] appearing in Eq. (10), then Eq. (11) becomes:

$$E_D = A + B[^1O_2]_R - jB[^1O_2]_I. \quad (13)$$

Accordingly, the fundamental fourier component of detector output in phase with the incident chopped radiation is $A + B[^1O_2]_R$ and the magnitude of the fundamental fourier quadrature component (phase angle $= \phi - 90°$) is $$|E_D| = B[^1O_2]_I. \quad (14)$$

Figure 3:
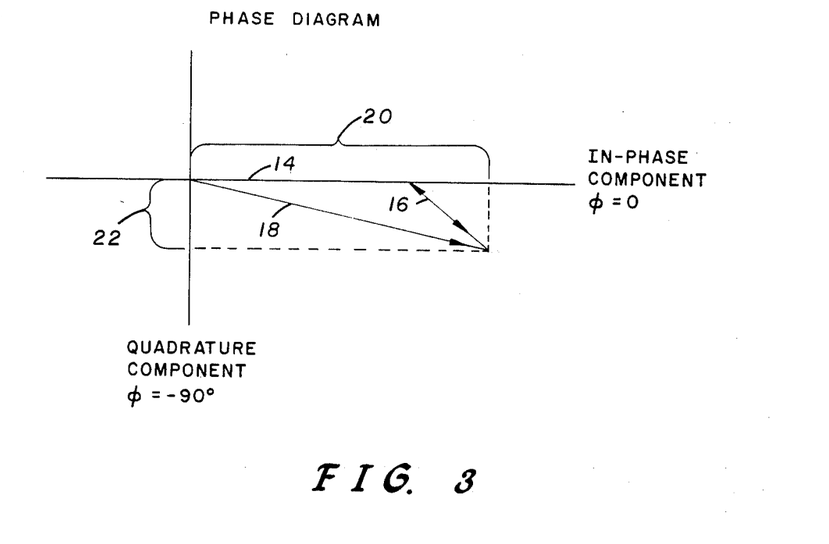
FIG. 3 is a phase diagram of the composite sensitizer fluorescence/singlet oxygen emission signal appearing in the 1.27 micron band.

Thus, the in-phase component is a mixture of the sensitizer fluorescence and the real component of the [¹O₂]-emission while the quadrature component (phase angle $\phi = -90°$) depends ONLY on the ¹O₂ emission. The relationship of the real and quadrature components of the composite emission in the 1.27 micron band is displayed graphically in FIG. 3, which contains a phase diagram of the composite signal. The horizontal axis of the phase diagram shows the in-phase or real component (phase $\phi = 0°$) and the vertical axis shows the quadrature or imaginary component (phase angle $\phi = 90°$). Since the sensitizer fluorescence (14) is essentially concurrent with the excitation light, its phase vector with appear at phase angle $\phi = 0°$ (e.g., the sensitizer fluorescence is in-phase with the chopped CW excitation signal). However, the singlet oxygen signal, as shown in the above equations, appears as a vector (16) having a phase delay (e.g., the singlet oxygen emission signal lags the sensitizer fluorescence 14). The sum of the sensitizer fluorescence vector 14 and the singlet oxygen emission vector 16 produces a resultant signal vector 18. The resultant signal vector can be divided into a real component (phase angle $\phi = 0°$) 20 and an imaginary component (phase angle $\phi = -90°$) 22. The real or in-phase component is the sum of the real sensitizer fluorescence component and the real singlet oxygen emission component. However, the imaginary or quadrature component 22 is only dependent on singlet oxygen emission. (The fact that the quadrature component is only dependent on the singlet oxygen emission has been demonstrated by Equation 14 above.) This phase difference is important in separating the ¹O₂ emission from the sensitizer fluorescence when chopping the CW excitation is used as the diagnostic means.

The present invention uses a signal processing means for determining the fundamental fourier components of the composite sensitizer/singlet oxygen signal and provides as output the magnitude of the quadrature component, i.e., the magnitude of the fundamental fourier signal 90° out of phase from the incident chopped CW excitation light. The invention uses a lock-in amplifier or synchronous detector to perform such signal processing. Separation of the ¹O₂ emission in this fashion requires that the *incident exciting light be chopped* to provide a reference signal for the lock-in amplifier. The lock-in output, in-phase and quadrature components, are thus synchronized to this reference. Earlier measurements of ¹O₂ emission by other investigators have employed a technique in which the *emission* is chopped, which although providing an improvement in the signal-to-noise ratio, is incapable of separating the two types of emission, yielding instead the sum of the two. For non-biological media such as carbon tetrachloride, this may be adequate since long singlet oxygen lifetimes are involved with correspondingly increased ¹O₂ emission levels relative to the sensitizer fluorescence. In biological media, however, the situation is drastically changed and in general the amplitude of the ¹O₂ emission is substantially exceeded by that of the sensitizer fluorescence.

Resolving the right hand side of Eq. (10) into its real and imaginary components, we obtain $$[^1O_2]_R = [T_1]_o \left[ \frac{1 - \omega^2\tau_T\tau_D}{(1 + \omega^2\tau_T^2)(1 + \omega^2\tau_D^2)} \right] \quad (15)$$

and $$[^1O_2]_I = [T_1]_o \left[ \frac{\omega(\tau_T + \tau_D)}{(1 + \omega^2\tau_T^2)(1 + \omega^2\tau_D^2)} \right]. \quad (16)$$

Figure 4:
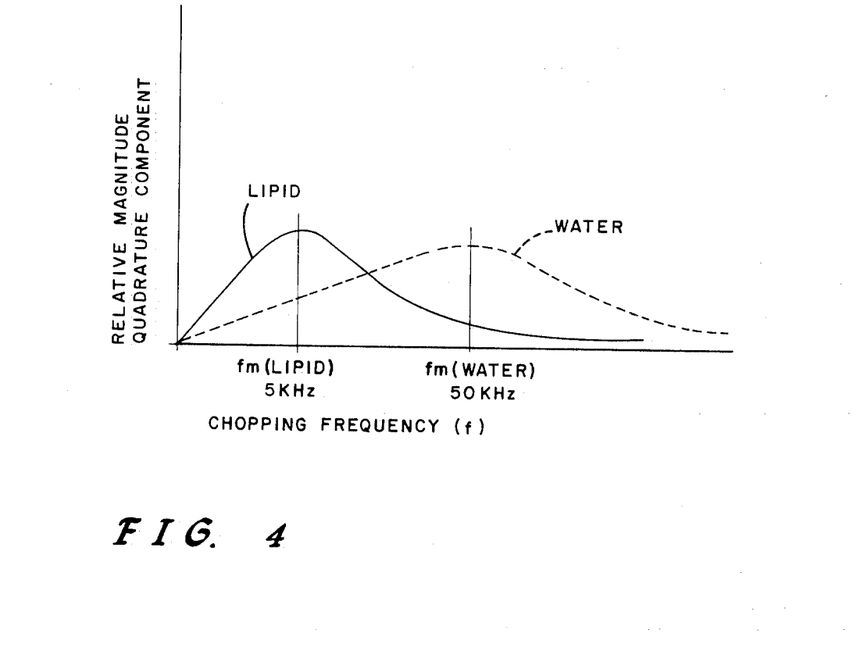
FIG. 4 is a plot of the relative magnitude of the singlet oxygen quadrature component as a function of chopping frequency ($f_c$) for lipid and aqueous media.

FIG. 4 shows a plot of $[^1O_2]_I$ as a function of the chopped frequency $f_c$ (note: $f_c = w/2\pi$, where w is angular frequency). The $[^1O_2]_I$ component reaches a maximum value at:

$$\omega_M = \left[ \frac{2}{(1+4\eta)^{\frac{1}{2}} + 1} \right]^{\frac{1}{2}} \left( \frac{1}{\tau_T + \tau_D} \right) \quad (17)$$

in which $$\eta = \left( \frac{2\tau_T \tau_D}{\tau_T^2 + \tau_D^2} \right)^2. \quad (18)$$

For a lipid environment (dominated by CH), $Y_T << Y_D$ and thus $\eta << 1$ with the consequence that $$w_m = \frac{1}{T_D} \quad (19)$$

or $$f_M = \frac{1}{2\pi T_D} \quad (20)$$

Under the condition $w = w_M$ it is to be noted that $[^1O_2]_R$ decreases to approximately $[T_1]_o/2$. However, this is relatively unimportant since the magnitude of this component will always be overshadowed by the sensitizer fluorescence in a biological environment. The quadrature component at this same frequency assumes a maximum value $[T_1]_o/2$.

Therefore, selecting the appropriate chopping frequency $f_c = f_M$ will maximize the singlet oxygen quadrature component. The chopping frequency $(f_c)$ for a particular medium is chosen in accordance with Equation (20) (e.g., $f_c = f_M = 1/(2\pi Y_D)$, where $Y_D$ equals the quenching time of singlet oxygen in the given medium). In a biological environment the essential components are predominantly water and lipid materials. The inventors have found, in accordance with Equation 20, that for a water medium the maximum singlet oxygen quadrature component appears when the chopping frequency $(f_c)$ is approximately 50 kHz; for a lipid medium the chopping frequency $(f_c)$ for a maximum singlet oxygen quadrature component will be approximately 5 to 10 kHz.

Figure 5:
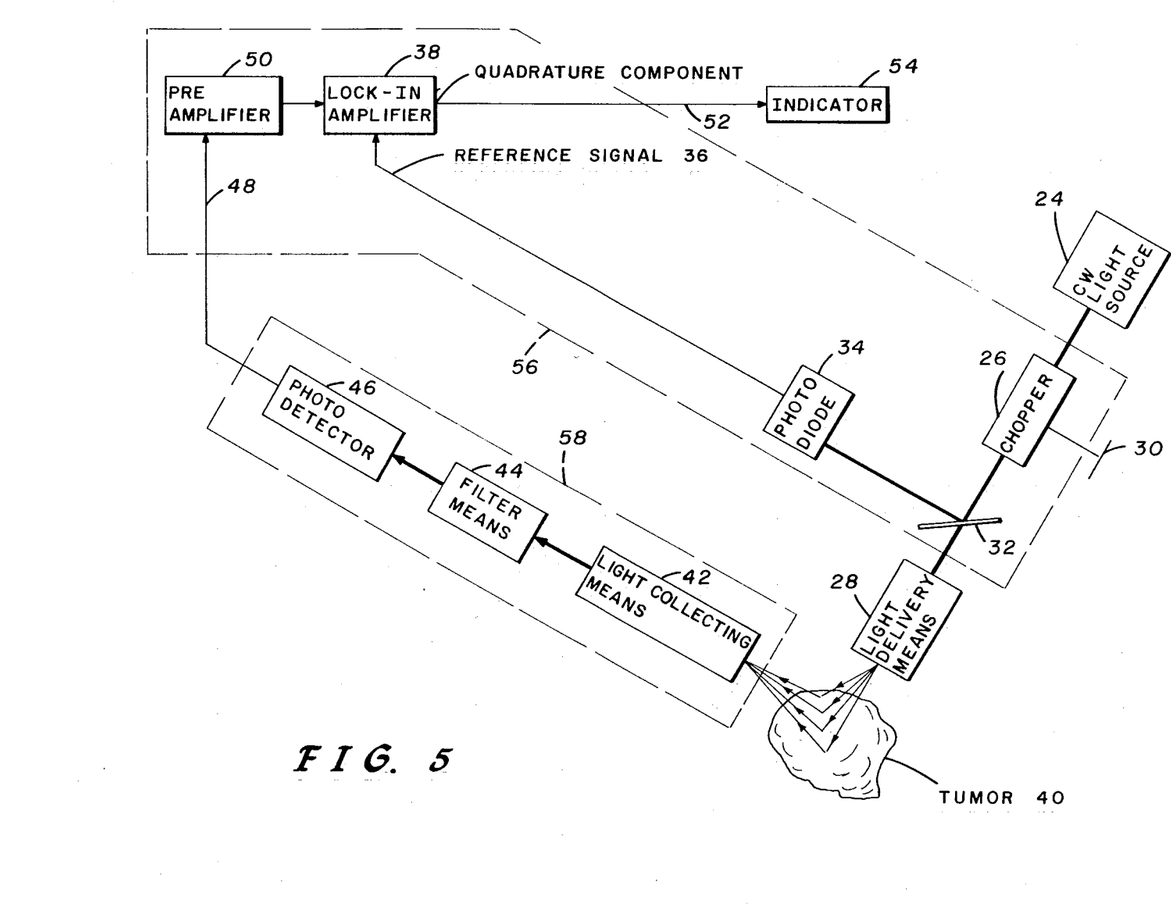
FIG. 5 illustrates, in block diagrammatic form, the invented apparatus used to process the composite sensitizer fluorescence/singlet oxygen emission signal so as to extract the singlet oxygen emission signal.

FIG. 5 is a block diagrammatic view of the apparatus in accordance with the present invention. A CW light source 24, which may be a laser is chopped by chopper 26 and directed by a light delivery means 28 onto the biological mass. The chopper may be a mechanical chopper, an acousto-optic modulator, or similar devices capable of chopping the excitation beam at a rate from 1 kHz to 100 kHz. The chopper 26 has adjustment 30 so that the chopping frequency $(f_c)$ can be set at particular values or scanned across a range of values. The light delivery means 28 used to direct the chopped CW excitation beam can be a lens arrangement or a fiberoptic link, as shall be discussed later in this application.

A beam splitter 32 and a photodiode 34 work in conjunction to produce a reference signal 36, which is used to synchronize the lock-in amplifier 38. Alternatively, an electrical signal produced directly by the chopping circuit can act as a reference signal 36, to synchronize the lock-in amplifier.

The biological mass or tumor 40 which has absorbed a photodynamic sensitizer, such as hematoporphyrin derivative or components thereof, and which is irradiated will emit a composite signal composed of a sensitizer fluorescent component and a singlet oxygen emission component. A light collecting means 42, which may be a lens arrangement or fiberoptic link, collects the light. The collected light is then filtered by filter means 44 which passes light in the singlet oxygen 1.27 micron emission band. (The inventors have used a bandpass filter having 3 db down points at 1.26 micron and 1.28 micron; however, any narrow bandpass filter which passes the 1.27 micron singlet oxygen emission signal will be adequate.) The filtered light is then directed to a photodetector 46 which converts the composite sensitizer fluorescence/singlet oxygen emission signal, both appearing in the 1.27 micron emission band, into an electrical signal 48. The inventors have found that a "fast" photodiode is necessary to temporally resolve the prompt sensitizer fluorescence and the delayed singlet oxygen emission. The detector should have a "Detector Time Decay Constant" of 0.2 microsecond (i.e., the return or decay response should fall off by 1/e in 0.2 microseconds and to less than 1% in 1 $\mu$sec). The inventors have found an Indium Gallium Arsenide/Indium Phosphide (InGaAs/InP) back-illuminated diode to be useful in this application.

The electrical signal 48 is amplified by preamplifier 50. The output of the preamplifier 50 is fed to lock-in amplifier 38. The inventors have used a EG&G PAR Model 124A lock-in amplifier, but other known lock-in amplifiers or synchronous detectors can be used as well. The lock-in amplifier 38 has as inputs the reference signal 36 and the output from preamplifier 50. The imaginary or quadrature component (phase angle $\phi = -90°$) is provided by the lock-in amplifier at output terminal 52. Indicator 54 connects to output terminal 52 and displays the magnitude of the quadrature signal which is directly proportional to the magnitude of the instantaneous singlet oxygen concentration generated in the biological mass 40 by photoradiation.

In operation, the lock-in amplifier 38, photodiode 34, beam splitter 32 and chopper 26 work in conjunction to produce the signal processing means 56 which extracts the singlet oxygen signal from the composite sensitizer fluorescence/singlet oxygen signal. The CW excitation beam is chopped at a frequency $(f_c)$ selected to maximize Equation 16 and produce the largest quadrature singlet oxygen signal for a particular case. The light collecting means 42, filter means 44, and photo detector 46, comprise an optical detecting means 58 for detecting the composite sensitizer fluorescence/singlet oxygen emission signal in the 1.27 micron singlet oxygen emission band and for generating a corresponding electrical signal 48. The signal processing means 56 then processes the composite signal 48 and provides as output the magnitude of the fundamental quadrature component.

As discussed previously, the quadrature component produced by the lock-in amplifier is dependent only on the singlet oxygen emission. However, it will be noted that a phase delay other than 90° can be used to isolate the singlet oxygen signal (e.g., 98°, 99°, 91°, 92°); however, the resulting signal will contain a small portion of the sensitizer fluorescent signal. As the phase difference between the sensitizer fluorescence and singlet oxygen emission approaches $-90°$, the singlet oxygen imaginary component is maximized. Therefore, in general, the signal processing means as taught by the present invention, processes the composite sensitizer fluorescence/singlet oxygen emission signal and separates the phase delayed singlet oxygen component from the sensitizer fluorescent component which is essentially in phase which the chopped CW incident light.

Figure 6:
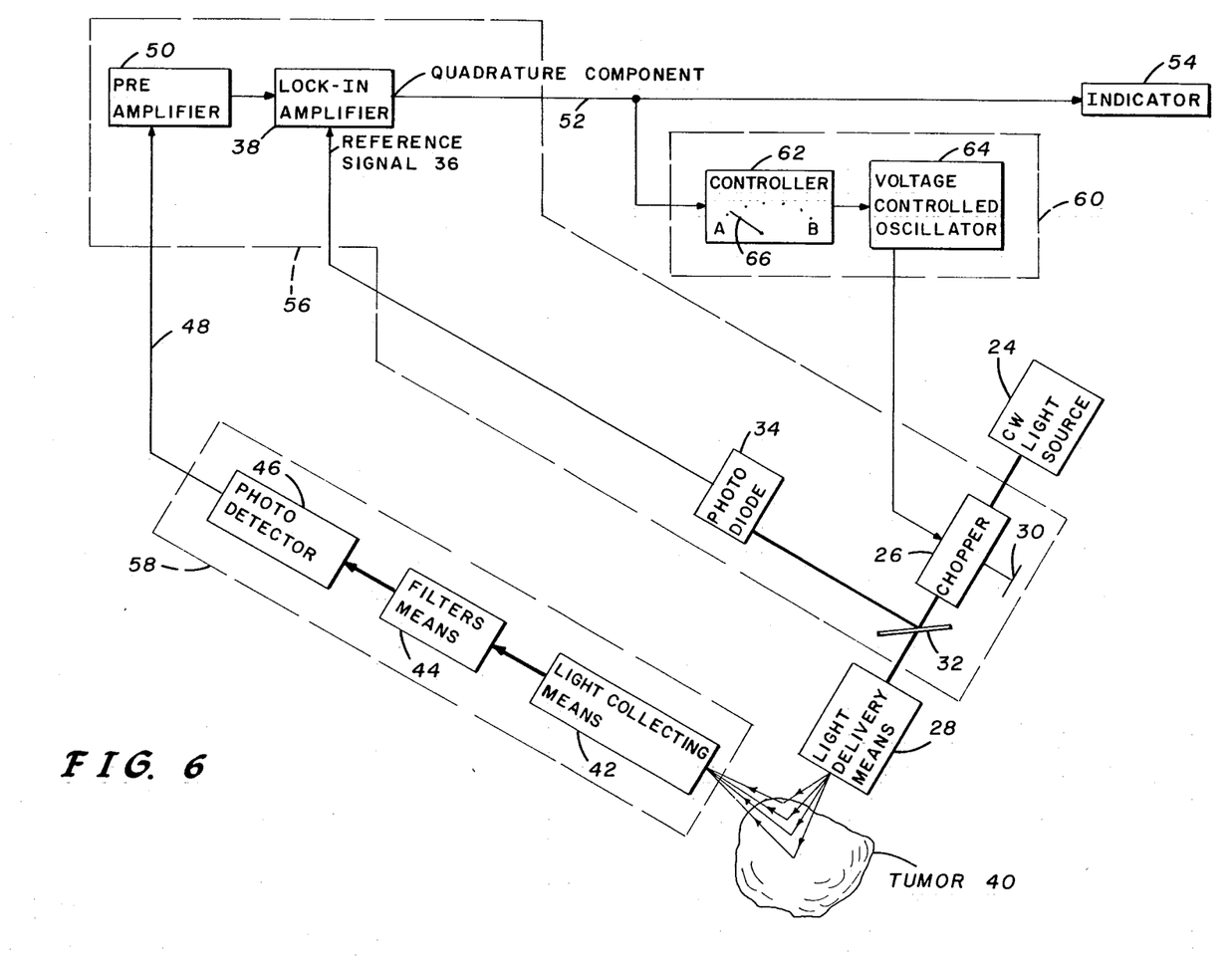
FIG. 6 illustrates, in block diagrammatic form, an embodiment of the present invention in which the chopping frequency ($f_c$) is automatically scanned across a frequency range.

FIG. 6 is a block diagrammatic view showing the invented apparatus operable in a scanning mode. As discussed earlier, the desired chopping frequency ($f_c$) needed to maximize the singlet oxygen quadrature component depends on the particular medium. For a complex biological mass or tumor, certain areas may be dominated by an aqueous environment and other areas may be dominated by a lipid environment. During a particular photoradiation therapeutic treatment, the concentration of singlet oxygen in an aqueous versus lipid environment may undergo change. Therefore, to obtain the maximum quadrature component in a complex biological environment, it is necessary to scan the chopping frequency ($f_c$) to determine the maximum quadrature signal. (Without such scanning, the quadrature component may appear to drop, indicating that less singlet oxygen is being produced, when in reality there has only been a shift from an area dominated by one environment to an area dominated by another environment or a shift in a particular area from domination by one solvent to domination by another.)

Figure 7:
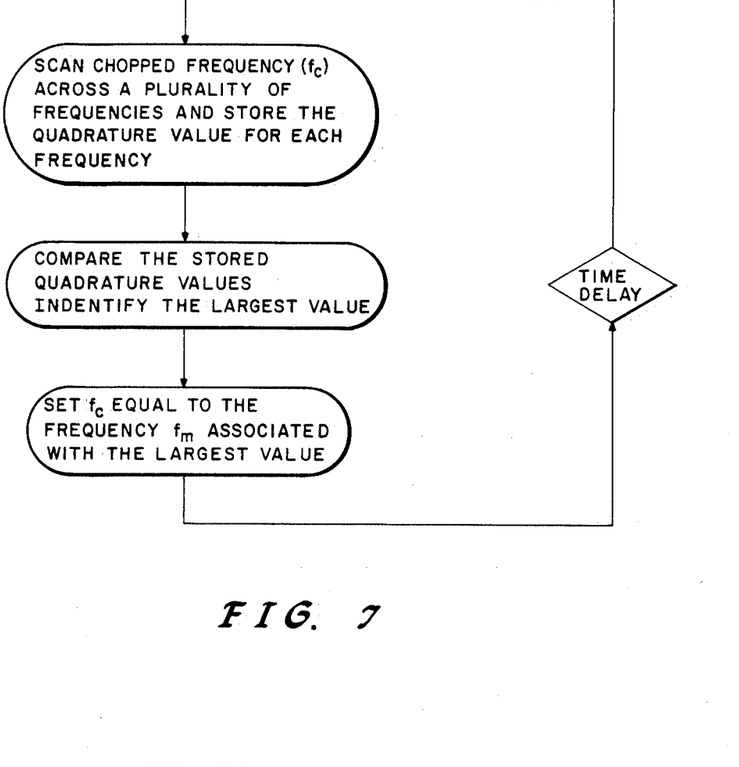
FIG. 7 is a flow chart showing the operation of a microprocessor controller used to scan the chopping frequency ($f_c$) and to analyze the resulting singlet oxygen quadrature component.

The scanning apparatus, shown in FIG. 6, generally includes: (1) an optical excitation means including a CW light source 24, a variable rate chopper 26 and a light delivery means 28; (2) an optical detection means 58, comprising a light collection means 42, a filter means 44, and a photodetector 46; (3) a signal processing means 56 generally including a preamplifier 50, a lock-in amplifier 38 to generate the quadrature signal 52. The lock-in amplifier is triggered by reference signal 36 generated by beam splitter 32 and photodiode 34; and, (3) a chopping frequency scanning means 60 which incorporates a controller 62 and a voltage controlled oscillator 64 which drives the variable rate chopper 26. The controller has a switch 66 which allows it to be operated either in the search mode or set to one of a plurality of possible positions. (A preset chopping frequency would be used if one were only interested in measuring the maximum singlet oxygen concentration generated in a particular environment). The controller 62 periodically scans the chopping frequency ($f_c$) across a plurality of frequencies in the range of 1 kHz to 100 kHz and stores the maximum quadrature value for each of said plurality of frequencies. The controller 62 then compares the stored values and locks the chopping frequency ($f_c$) at that frequency which had provided the largest quadrature component. The controller 62 maintains that chopped frequency ($f_m$) for a set period of time and then again enters the scanning mode to redetermine the frequency for a maximum $^1O_2$ signal. (The controller 62 can also be programmed to select values other than the maximum quadrature component; for instance, the controller could be programmed to tune the signal processing circuit to a chopping frequency which produces a ½ maximum quadrature value.) The controller 62 can provide a control voltage to a voltage controlled oscillator 64 which generates a chopping frequency ($f_c$) used to control the chopper 26. The controller 62 may be a microprocessor circuit of contemporary design to carry out the functions described above and as also outlined in the flow chart of FIG. 7.

It will be noted that it is within the scope of the invention to either manually or automatically scan the chopping frequency ($f_c$) to obtain the desired quadrature signal. Similarly, the chopping schedule may also be managed either manually or automatically. For instance, the apparatus shown in FIG. 5 can be manually tuned to the desired chopping frequency, by the operator adjusting knob 30, as the intensity of the quadrature value is noted on indicator 54. It is also contemplated that for a particular applications a preset chopping frequency ($f_c$) will be adequate if the maximum singlet oxygen quadrature signal is only required for particular medium. It is also to be realized that the choice of the chopping frequency ($f_c$) allows one to separate the maximum singlet oxygen quadrature component produced in different media, thereby exploring the water/lipid concentration in a complicated biological environment.

It will also be noted that the CW light source need not be chopped continuously but only when singlet oxygen is measured. Since chopping the CW excitation reduces the amount of power transmitted to the photodynamic sensitizer, it may be advantageous to either manually or automatically initiate chopping only when periodic singlet oxygen measurements are being made. It is therefore within the contemplation of the inventors to use controller 62 to control the variable rate chopper 26 in such a manner that the CW excitation is only chopped during periods of periodic measurements of singlet oxygen concentration. If the controller 62 is designed from known microprocessor circuitry, this function can be accomplished by a separate subroutine which initiates chopping and singlet oxygen emission measurements in a controlled manner.

Figure 8:
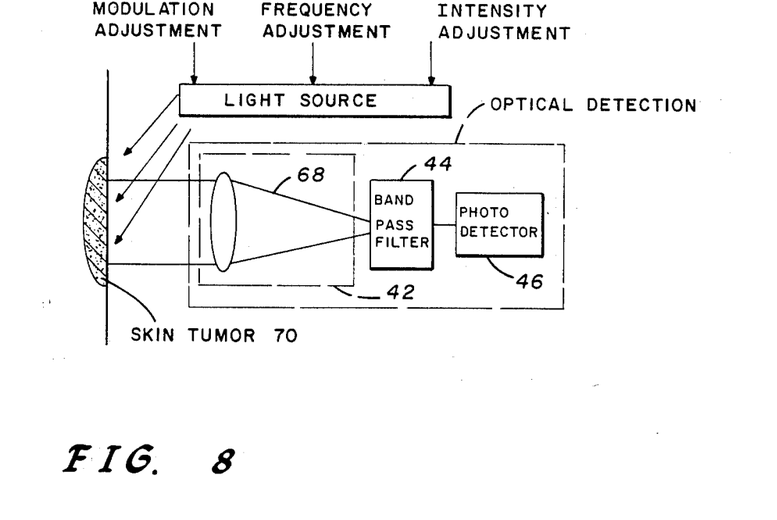
FIG. 8 is the light collecting means for collecting the composite signal emitted from a surface or skin tumor.
Figure 9:
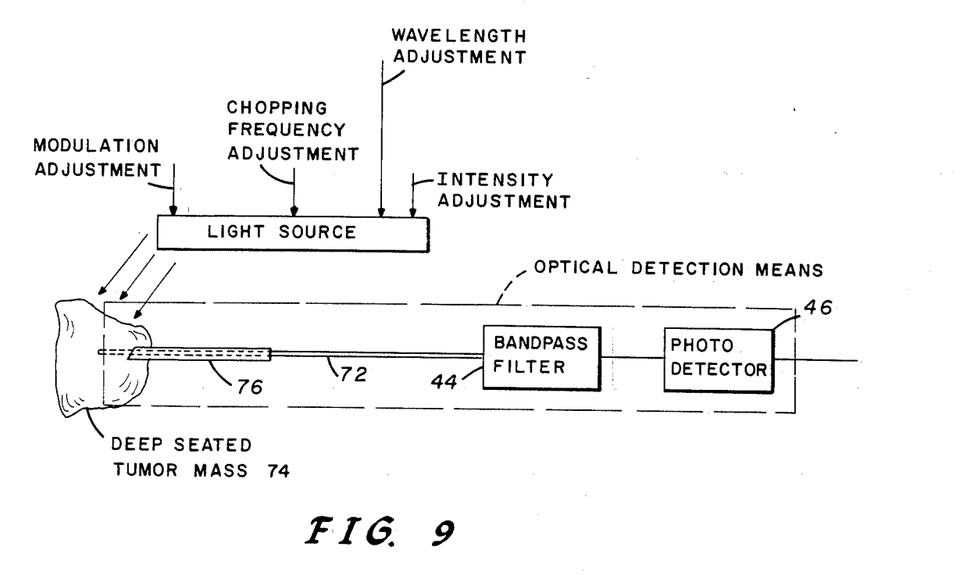
FIG. 9 is the light collecting means for collecting the composite signal emitted from a deep seated tumor mass.
Figure 10:
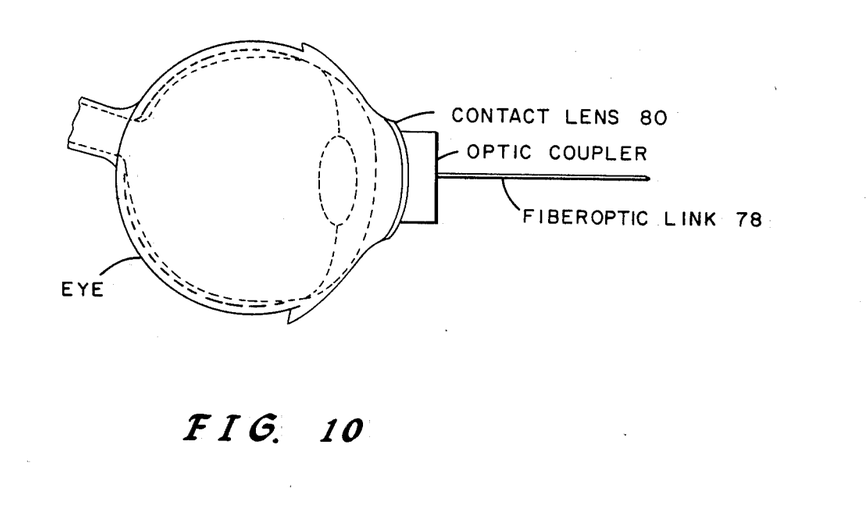
FIG. 10 is the light collecting means for collecting the composite signal emitted from an ocular tumor.

FIGS. 8, 9 and 10 show various light collecting means 42 and a light delivery optical means 28 contemplated by the inventors. In FIG. 8, the lens arrangement 68 collects light emitted by a surface or skin tumor 70 and focuses emitted light through filter 44 and onto the photodetector 46. FIG. 9 shows an alternative embodiment used in the treatment of deep seated tumors. A fiberoptic wave guide 72 is inserted into the tumor mass 74 and directs collected light to the filter 44. The fiberoptic wave guide 72 can be inserted into tumor mass 74 through a hollow hypodermic needle 76. A single fiberoptic probe could be used to direct the chopped CW excitation light into the tumor mass and also to collect and transmit collected emissions to the photodetector 46. FIG. 10 shows an alternative embodiment used in the treatment of ocular tumors. A fiberoptic link 78 is optically coupled to a contact lens 80 rather than inserted into the tumor area. The contact lens arrangement generally contains a contact lens which is placed over the cornea and optically coupled by known coupling means 81 to a fiberoptic link. The contact lens fiberoptic link combination collects the emitted light and transmits it to the optical detection means.

The current invention has many applications where singlet oxygen is measured in a biological environment or other environments where the singlet oxygen emission signal is masked by the sensitizer fluorescent signal. Applicants have discovered that one such application is in monitoring the effectiveness of photochemotherapy. Current photochemotherapy treatment involves intravenous injection of the patient with a photodynamic sensitizer, e.g., hematoporphyrin derivative or components thereof. After two to three days the sensitizer has been selectively retained by the tumor tissue. CW light is then used to excite the hematoporphyrin derivative to its triplet state to produce singlet oxygen within the malignant tissue. The therapeutic light may penetrate directly through the patient's skin into the tumor area if the tumor is located relatively close to the surface. For deep-seated or large tumors, a system employing fiber-optics may be used which allows delivery of the light to any desired depth within the tumor. The therapeutic light can also be delivered by various types of endoscopes to the cervix, bronchus, bladder, etc.

In prior art photoradiation therapy light delivery systems, the physician must guess the correct therapeutic light dosage. If the dosage is too high, normal tissue will experience necrosis; and, if the dosage is insufficient, the tumor will not be destroyed. Since the physician has no way of knowing the rate at which oxygen is being delivered to the tissue or the magnitude of the photodynamic sensitizer concentration, it is impossible to predict the effect of a given therapeutic light dosage. If the light dosage is too intense, local oxygen may be depleted more rapidly than is provided to the tissue and no additional singlet oxygen will be generated for any increase in intensity or duration of the light dosage. The only adequate way to prescribe the correct therapeutic light dosage therefore is by direct monitoring of the level of singlet oxygen produced.

The present invention provides a means for direct monitoring of the singlet oxygen concentration produced during photochemotherapy. A continuous CW light source can illuminate the biological mass and can be periodically chopped according to a predetermined program and the singlet oxygen signal processed, as taught by the present invention. The singlet oxygen quadrature level displayed by indicator 54 (see FIGS. 5 and 6) is a direct measure of singlet oxygen concentration. If the quadrature signal drops significantly, it indicates the need to modify the excitation light dosage (i.e., local oxygen depletion has probably occurred). The physician can adjust the intensity, duration, frequency or modulation of the excitation beam to maximize the singlet oxygen quadrature component, and thereby insure the effectiveness of photochemotherapy. Also by recording the quadrature component as a function of chopping frequency ($f_c$), a physician can determine properties of the tumor mass. In short, the present invention gives the physician a means for monitoring, in real time, the amount of singlet oxygen generated in the tumor mass and provides a measure of treatment effectiveness.

Obviously many modifications and variations of the present invention are possible in light of the above teachings. It is therefore to be understood that within the scope of the appended claims the invention may be practiced otherwise than is specifically described.

What is claimed and desired to be secured by letters patents of the United States is:

1. An apparatus for detecting singlet oxygen emission produced during photoradiation:
   an optical excitation means for illuminating a particular portion of a medium containing a photodynamic sensitizer with chopped optical radiation of a wavelength capable of at least causing generation of a singlet oxygen emission;
   an optical detection means for collecting light emitted from said medium and for detecting a composite optical signal in a 1.27 micron singlet oxygen emission band, the band having a bandwidth including a sensitizer fluorescent emission signal component and a singlet oxygen emission signal component that is out of phase with the fluorescent signal component;
   a signal processing means, operably associated with said optical detection means, for processing said composite optical signal and for separating said singlet oxygen signal component from said sensitizer fluorescent signal component by utilizing a difference in phase between the two signal components; and,
   a responsive means, operably associated with said signal processing means, for providing an indication of the magnitude of said singlet oxygen signal component.

2. The apparatus of claim 1, wherein said signal processing means includes means for determining the fundamental fourier component of said composite signal, and for outputting to said responsive means the magnitude of the component of said fundamental component that is out-of-phase from said chopped optical radiation.

3. The apparatus of claim 2, wherein said signal processing means includes means for separating a singlet oxygen component that is about 90° out of phase from said chopped radiation.

4. The apparatus of claim 1, wherein said signal processing means comprises a lock-in amplifier, and means for triggering the lock-in amplifier in sequence with said chopped optical radiation.

5. The apparatus of claim 4, further including:
   a chopping frequency scanning means for scanning the chopping frequency of said chopper across a plurality of frequencies, and for causing the chopper to chop at a chopping frequency corresponding to the maximum singlet oxygen component signal processed by said signal processing means for each of said plurality of chopping frequencies.

6. The apparatus of claim 5, wherein said chopping frequency scanning means includes means for scanning periodically the plurality of chopping frequencies to periodically select a desired chopping frequency.

7. The apparatus of claim 1, wherein said signal processing means comprises a lock-in amplifier.

8. The apparatus of claim 7, wherein said lock-in amplifier includes means for outputting the magnitude of the component of said fundamental component that is about 90° out-of-phase with said chopped optical radiation.

9. The apparatus of claim 1, wherein said optical excitation means includes a chopper that has a variable frequency control that may be set to chop at a frequency $f_c = 1/(2\pi Y_D)$, where $Y_D$ equals the quenching time of singlet oxygen in a medium selected for photoradiation.

10. The apparatus of claim 1, wherein said optical excitation means includes:
    a light source means for producing optical radiation;
    a chopper, optically coupled to said light source for chopping said optical radiation; and,
    a light delivery means, optically coupled to said chopper, for directing a chopped optical radiation onto said biological medium.

11. The apparatus of claim 10, wherein said chopper has a variable frequency control that may be set to control the chopper at a chopping frequency $f_c = 1/2\pi Y_D$, where $Y_D$ equals the quenching time of singlet oxygen in a medium selected for photoradiation.

12. The apparatus of claim 11, wherein said chopping frequency for a water medium is approximately 50 kHz.

13. The apparatus of claim 11 wherein said chopping frequency for a lipid medium is in the range 5 to 10 kHz.

14. The apparatus of claim 10, wherein said chopper includes means for controlling the chopper frequency and for maximizing the singlet oxygen component indicated by said responsive means.

15. The apparatus of claim 10, wherein said chopper includes a chopping frequency adjusting means for adjusting the chopping frequency of said chopper, said adjusting means including means for scanning said chopping frequency across a plurality of frequencies, and means for selecting a chopping frequency corresponding to the maximum singlet oxygen component signal magnitude processed by said signal processing means from said plurality of chopping frequencies.

16. The apparatus of claim 1, wherein said optical detection means includes:
 a light collecting means for collecting light emitted from biological media;
 a filter means for blocking light outside of the singlet oxygen 1.27 micron emission band; and,
 a photodetector means for converting the composite sensitizer fluorescence/singlet oxygen emission signal appearing in the 1.27 micron singlet oxygen band into an electrical signal.

17. The apparatus of claim 16, wherein said filter means is a bandpass filter centered at 1.27 microns having 3 dB downpoints at 1.26 microns and 1.28 microns.

18. The apparatus of claim 16, wherein said photodetector means has a decay response which falls off by 1/e in 0.2 microseconds and to less than 1% in 1 microsecond.

19. The apparatus of claim 18, wherein said photodetector means is an Indium Gallium Arsenide/Indium Phosphide (InGaAs/InP) back/illuminated diode.

20. The apparatus of claim 16, wherein said light collecting means is a lens arrangement.

21. The apparatus of claim 16, wherein said light collecting means is a fiberoptic light guide adapted for insertion into said biological medium.

22. The apparatus of claim 16, wherein said light collecting means is a fiberoptic link optically coupled to a contact lens to be worn on a patient's eye during treatment.

23. A therapeutic light dosimetry procedure for use in the photoradiation therapeutic treatment of a living body, wherein said living body is injected with a photosensitive dye capable of generating singlet oxygen in said living body, said dosimetry procedure comprising the steps of:
 irradiating the injected photosensitizing dye with a certain light dosage, causing said photosensitizing dye to energize available local oxygen existing in said living body to generate singlet oxygen;
 detecting the emission produced from singlet oxygen radiative decay in the 1.27 micron singlet oxygen emission band from a plurality of different emissions in the same band that are caused by the light in the step of irradiating;
 determining the magnitude of the detected emissions to indicate the extent available local oxygen depletion has reduced singlet oxygen production.

24. A therapeutic light dosimetry procedure for use in the photoradiation therapeutic treatment of a living body, wherein said living body is injected with a photosensitizing dye capable of generating singlet oxygen in said living body, said dosimetry procedure comprising the steps of:
 generating singlet oxygen by photoradiating the injected photosensitizing dye with light;
 detecting the emission produced from singlet oxygen decay in the singlet oxygen 1.27 micron emission band from a plurality of different emissions in the same band that are caused by the photoradiation in the step of generating;
 determining the magnitude of the detected singlet oxygen emission; and,
 indicating the magnitude of detected singlet oxygen emission generated for the particular light dosage used in the step of generating.

25. A photoradiation procedure comprising:
 injecting a photosensitizing dye capable of generating singlet oxygen into a living body;
 generating singlet oxygen by photoradiating the injected photosensitizing dye;
 detecting the emission produced from singlet oxygen radiative decay in the singlet oxygen 1.27 micron emission band from a plurality of different emissions in the same band that are caused by the photoradiation in the step of generating;
 determining the magnitude of the detected singlet oxygen emission; and,
 adjusting the photoradiation in accordance with the magnitude of said singlet oxygen emission.

26. A photoradiation procedure comprising:
 injecting a photosensitizing dye capable of generating singlet oxygen into a living body;
 irradiating the injected photosensitizing dye with optical energy, causing said photosensitizing dye to energize available local oxygen existing in said living body to generate singlet oxygen;
 detecting the emission produced from singlet oxygen radiative decay in the 1.27 micron singlet oxygen emission band from a plurality of different emissions in the same band that are caused by the optical energy in the step of irradiating;
 determining the magnitude of the detected singlet oxygen emission; and,
 adjusting the optical energy in accordance with the magnitude of said detected emission, to compensate for reduction in said available local oxygen which causes reduced singlet oxygen concentration.

27. A method for directly monitoring the singlet oxygen level produced during photoradiation therapy, said method comprising the steps of:
 illuminating a portion of a biological medium containing a photodynamic sensitizer with chopped optical radiation having a wavelength which will cause the sensitizer to fluoresce and cause singlet oxygen decay emissions out of phase with the fluorescence;
 collecting light emitted from said biological medium;
 generating a composite sensitizer fluorescence/singlet oxygen emission signal from the collected light;
 processing said composite sensitizer fluorescence/singlet oxygen emission signal and separating the singlet oxygen component from the sensitizer fluorescent component based on their relative phase difference; and,
 indicating the magnitude of said singlet oxygen signal component.

28. The method of claim 27, wherein said processing step includes the steps of determining the fundamental fourier component of said sensitizer fluorescence/singlet oxygen emission signal and determining the magnitude of the component of said fundamental component that is out-of-phase with said chopped optical radiation.

29. The method of claim 28, wherein said separating step includes the step of separating the component that is about 90° out of phase with said chopped optical radiation.

30. The method of claims 28 or 29, further including the steps of:
scanning the chopping frequency of said optical radiation across a plurality of frequency values; and,
selecting the chopping frequency which provides the largest singlet oxygen signal component.

31. The method of claim 30, further including the step of periodically scanning the chopping frequency and selecting the chopping frequency which produces the largest singlet oxygen signal component.

32. The method of claim 28 or 29, further including the step of:
tuning the chopping frequency of said optical radiation to a particular value depending on the characteristics of the biological medium.

33. The method of claim 32, wherein said chopping frequency is set to approximately 50 kHz to detect singlet oxygen emission produced in an aqueous portion of the biological medium.

34. The method of claim 32, wherein said chopping frequency is tuned within a band of 5–10 Khz to detect the signal level attributable to the maximum signal oxygen emission produced in a lipid component of a biological medium.

35. The method of claim 27, further involving the step of chopping the optical excitation during periods when the singlet oxygen level is being measured.

36. The method of claim 27, further involving the step of adjusting the intensity of said optical radiation to increase or decrease the singlet oxygen level.

37. The method of claim 27, further involving the step of adjusting the frequency of said optical radiation to increase or decrease the singlet oxygen level.

38. The method of claim 27, further involving the step of adjusting the modulation of said optical radiation to increase or decrease the singlet oxygen level.

* * * * *

UNITED STATES PATENT AND TRADEMARK OFFICE
CERTIFICATE OF CORRECTION

PATENT NO. : 4,576,173
DATED : March 18, 1986
INVENTOR(S) : Parker et al.

It is certified that error appears in the above—identified patent and that said Letters Patent is hereby corrected as shown below:

In the title delete "Instanteous" and substitute therefor -- Instantaneous --.

In the references, Column 2, line 9, delete "Clanton" and substitute therefor -- Clayton --.

In the specifications:

Column 11, line 17, delete "$Y_T \ll Y_D$" and substitute therefor -- $\tau_T \ll \tau_D$ --.

Column 11, line 37, delete "$(2\pi Y_D)$, where $Y_D$" and substitute therefore -- $(2\pi \tau_D)$, where $\tau_D$ --.

In the claims:

Column 16, line 49, delete "$(2\pi Y_D)$ and substitute therefor -- $(2\pi \tau_D)$ --.

Column 16, line 63, delete "$Y_D$, where $Y_D$" and substitute therefor -- $\tau_D$, where $\tau_D$ --.

Signed and Sealed this

Fourth Day of November, 1986

[SEAL]

Attest:

DONALD J. QUIGG

Attesting Officer

Commissioner of Patents and Trademarks